United States Patent [19]

Byers

[11] Patent Number: 4,922,049
[45] Date of Patent: May 1, 1990

[54] SYNTHESIS OF CIS-OLEFINS
[75] Inventor: Jim D. Byers, Bartlesville, Okla.
[73] Assignee: Phillips Petroleum Company, Bartlesville, Okla.
[21] Appl. No.: 297,640
[22] Filed: Jan. 13, 1989
[51] Int. Cl.$^5$ .................. C07C 1/20; C07C 1/253
[52] U.S. Cl. .................. 585/327; 585/600; 585/609
[58] Field of Search .................. 585/327, 600, 629
[56] References Cited

U.S. PATENT DOCUMENTS

| | | | |
|---|---|---|---|
| 3,798,273 | 3/1974 | Cargill | 260/593 R |
| 3,932,616 | 1/1976 | Meresz | 424/84 |
| 3,940,425 | 2/1976 | Eiter | 585/642 |
| 3,948,803 | 4/1976 | Carney | 252/429 R |
| 4,006,065 | 2/1977 | Meresz | 204/59 R |
| 4,016,220 | 4/1977 | Wilheim | 260/683 D |
| 4,018,844 | 4/1977 | Meresz | 260/677 R |
| 4,609,498 | 9/1986 | Banasiak | 260/410.9 R |
| 4,740,627 | 4/1988 | Byers | 568/469.9 |
| 4,749,818 | 6/1988 | Byers | 585/324 |

OTHER PUBLICATIONS

*Comprehensive Org. Chem.,* vol. 3 (Perqamon Press, New York).
Gibson et al, *J. Org. Chem.,* 41:791 (1976).
Kirk-Othmer, Encyclopedia of Chemical Technology, vol. 12, 3rd ed. (Wiley & Sons, New York), pp. 39-40.
Cargill R. L. et al., Synthesis of Housefly Sex Attractant, J. Org. Chem. 37:3971 (1972).
Abe, K. et al, Bulletin of Chem. Soc. Japan 50 (10):2792 1977.
Gribble, G. W. et al., JCS Chem. Comm. 1973, pp. 735-736.
Ho, T. L. et al, Can. J. Chem., vol. 52, 1974, pp. 1923-1924.
Apsimon, J. The Total Synthesis of Natural Products, vol. 4, pp. 20-27.
Henrick, C.A., The Synthesis of Insect Sex Pheromones, Tetrahedron Report No. 34, vol. 33, pp. 1845-1889, (Pergamon Press).

*Primary Examiner*—Curtis R. Davis
*Attorney, Agent, or Firm*—Hal Brent Woodrow

[57] ABSTRACT

A process for the synthesis of cis-olefins from cis-olefinic alcohols consisting essentially of the following steps:

(a) reacting a cis-olefinic alcohol with a source of an alkali metal ion selected from the group consisting of lithium and sodium ions to form a first reaction product, (b) then contacting said thus formed first reaction product with a sulfonyl halide compound to form a second reaction product, (c) then containing said thus formed second reaction product with an alkyl magnesium compound and a cuprous salt to form a third reaction product comprising a cis-olefin wherein said steps are carried out in a suitable organic solvent.

21 Claims, No Drawings

4,922,049

SYNTHESIS OF CIS-OLEFINS

FIELD OF INVENTION

This invention relates generally to the synthesis of cis-olefins.

BACKGROUND OF THE INVENTION cis-olefins are an important source of pharmacological and biological compounds such as pheromones. Unfortunately, the synthesis of cis-olefins is a very difficult and expensive process because of the tendency of the beginning reaction products to isomerize into inactive or inhibitory trans-isomers. An example of a simple cis-olefin which has proven difficult to produce economically is cis-9-tricosene (Z-9-tricosene).

cis-9-tricosene is a known pheromone and is an important attractant used to control flies in cattle and poultry production. In order to make this compound readily available for use in insect control a variety of chemical syntheses have been developed. These syntheses involve (1) classical types of organic syntheses utilizing alkynes, phosphonium salts, ketone reductions with hydrazine (Huang-Minlon type reductions), ozonolysis of 1,5-cyclooctadiene, sulfone coupling, or borane coupling, (2) syntheses utilizing metathesis chemistry, (3) syntheses using electrochemical coupling of carboxylic acids, and (4) syntheses utilizing Grignard coupling of various erucyl and oleyl derivatives with the appropriate Grignard reagents. More recent syntheses involve (1) coupling of 1-bromo-2-phenylthioethenes with Grignard reagents in the presence of palladium or nickel catalysts, (2) reductions of certain dialkylated tosylmethyl isocyanides, (3) catalytic ring-opening of dihydropyran by certain Grignard reagents, and (4) condensation of certain Grignard reagents with the appropriate aldehydes to produce alcohols that can be dehydrated to give a mixture of alkenes containing the tricosene product.

Many of the more classical syntheses require the use of alkynes or Wittig reagents to obtain the desired cis-stereochemistry present in the housefly pheromone. Although these reagents produce cis-9-tricosene in high purity, their use in large scale production of pure cis-9-tricosene is prohibitively expensive. Currently, the most economical synthesis of cis-9-tricosene is achieved by coupling oleyl bromide with N-amylmagnesium bromide in tetrahydrofuran at 0° C.–5° C. using lithium chlorocyanocuprate, which is toxic.

Thus, it would be a significant contribution to the art to develop an alternative chemical synthesis for cis-olefins such as cis-9-tricosene which utilizes economical, less toxic reagents.

It would also be advantageous if the alternate process for the synthesis of cis-olefins were simple, and were characterized by easy to scale-up reactions which did not require multiple reaction vessels.

It would additionally be advantageous if the process for the synthesis of cis-olefins did not require the isolation or purification of intermediates between chemical synthesis steps.

It is an object of this invention to provide an economical, less toxic process for the synthesis of cis-olefins.

It is also an object of this invention to provide a simple, easy to scale-up process for the synthesis of cis-olefins which does not require multiple reaction vessels.

It is a further object of this invention to provide a process for the synthesis of cis-olefins which does not require the isolation or purification of the intermediates produced in the reaction.

It is a further object of this invention to provide a process for the synthesis of cis-9-tricosene.

Other aspects, objects, and several advantages of this invention will be apparent from the foregoing specifications, example, and claims.

SUMMARY OF THE INVENTION

In accordance with the present invention, I have discovered a process for the synthesis of a cis-olefin from a cis-olefinic alcohol consisting essentially of the following steps:
(a) reacting a cis-olefinic alcohol with a source of an alkali metal ion selected from the group consisting of lithium and sodium ions to form a first reaction product,
(b) then contacting said thus formed first reaction product with a sulfonyl halide compound to form a second reaction product,
(c) then contacting said thus formed second reaction product with and a cuprous salt and an alkyl magnesium compound to form a third reaction product comprising a cis-olefin wherein said steps are carried out in a suitable organic solvent.

DETAILED DESCRIPTION OF THE INVENTION

In accordance with one embodiment of this invention, cis-olefins are produced by
(1) deprotonation of a cis-olefinic alcohol to form a lithium or sodium salt followed by
(2) the formation of a sulfonate ester and
(3) the alkylation of the sulfonate ester with an alkylmagnesium compound and a cuprous salt, an alkylating catalyst.

To produce a cis-olefin, one need only begin with a cis-olefinic alcohol having a hydroxyl group at the desired site or sites of alkylation and choose an appropriate alkylmagnesium compound having the desired alkyl group.

Appropriate cis-olefinic alcohols for use in the process of this invention are non-conjugated, non-cumulated, non-enolic (without a double bond adjacent to a hydroxyl group) cis-olefinic alcohols. The cis-olefinic alcohols can also contain more than one double bond. A cis-olefinic alcohol with more than one double bond can be employed with a double bond allylic to the hydroxyl group if the allylic double bond position is inconsequential in the final cis-olefin because said allylic double bond may shift position. Although cis-olefinic allylic alcohols may be suitable for this process, they are not recommended because of the tendency for allylic bonds to shift with the resultant isomerization to trans-olefinic alcohols. The cis-olefinic alcohols can also include glycols and polyols, however, each hydroxyl may serve as a site of alkylation. The carbon chain length of the suitable cis-olefinic alcohol is only limited by the solubility of the cis-olefinic alcohol with regard to this process. A few cis-olefinic alcohols suitable for the practice of this invention include, but are not limited to, those selected from the group consisting of oleyl alcohol, cis-9-tetradecen-1-ol, cis-7-tetradecen-1-ol, cis-11-tetradecen-1-ol, and cis-5-decen-1-ol.

The first step of the process of the present invention is a deprotonation reaction of a cis-olefinic alcohol with a source of an alkali metal ion selected from the group consisting of lithium and sodium ions. The first reaction product would comprise an alkoxide which can be formed utilizing reagents and techniques known to those of skill in the art. Suitable sources of alkali metal ions include, but are not limited to, alkali metal ion sources selected from the group consisting of sodium metal, lithium metal, alkyllithium, alkylsodium, aryllithium, and arylsodium. The presently preferred source of alkali metal ions is an alkyllithium compound selected from the group consisting of phenyllithium, butyllithium, and methyllithium. It is presently preferred that the temperature at which deprotonation is performed should be maintained between about $-70°$ C. and about 50° C., more preferably between about $-10°$ C. and about 50° C. The stoichiometric ratio of cis-olefinic alcohol hydroxyl groups to the alkali metal ions may range from about 1:0.25 to about 1:1.5. Preferably, it will range from about 1:1 to about 1:1.1. Time is not a critical factor for reacting the cis-olefinic alcohol to form a lithium or sodium alkoxide and may vary depending upon the temperature and concentration of reactants; generally the reaction should be allowed to reach substantial completion before the next step is begun. However, the reaction will go to completion almost as quickly as the source of alkali metal ions is mixed with the cis-olefinic alcohol.

The second step of the process of the present invention is the reaction of the first reaction product, said alkoxide with a sulfonyl halide compound to form a sulfonate ester. Sulfonyl halide compounds suitable for this synthesis process can be selected from the group consisting of alkyl sulfonyl halides and aryl sulfonyl halides wherein the sulfonyl halide will not interfere with the alkylation in the third step. For the purpose of this specification and claims, alkyl sulfonyl halides shall also include triflates including, but not limited to, trifluoromethanesulfonyl halides. Preferred sulfonyl halide compounds include, but are not limited to, those selected from the group consisting of p-toluenesulfonyl halides, p- and o-toluenesulfonyl halides, trifluoromethane sulfonyl halide, methanesulfonyl halide, and benzene sulfonyl halide. The halides which can be used in sulfonyl halide compounds are selected from the group consisting of chloride and bromide. The most preferred sulfonyl halide compounds are p-toluenesulfonyl chloride and benzene sulfonyl chloride.

The reaction of the first reaction product, alkoxide with the sulfonyl halide compound to form the sulfonate ester, can take place under a wide variety of reaction conditions. Generally the reaction temperature will be in the range of about 0° C. to about 70° C. Preferably the reaction temperature is in the range of about 30° C. to about 60° C. In this step of the process of the present invention, pressure is generally not critical, but will generally be in the range of about 0 psig to about 2,000 psig. Preferably the pressure is in the range of about 1 psig to about 25 psig.

The time of reaction for reacting sulfonyl halide compound with a first reaction product to form a sulfonate ester will depend upon the desired degree of conversion, the reaction temperature and concentration of sulfonyl halide and alkoxide, but will generally be that time needed for the reaction to reach substantial completion before the next step is begun in the range of 1 hour. Preferably the reaction time is in the range of about 1 hour to about 24 hours.

The third step in this synthesis process is the reaction of the second reaction product with an alkylmagnesium compound and a cuprous salt, an alkylating catalyst, to form a third reaction product comprising a cis-olefin. The alkylmagnesium compound may be selected from the group consisting of dialkylmagnesium and alkylmagnesium halide wherein the halide of said alkylmagnesium halide is selected from the group consisting of iodide, bromide, and chloride. Presently, preferred for the practice of this process are alkylmagnesium halides selected from the group consisting of alkylmagnesium bromide and alkylmagnesium chloride. The alkylmagnesium compounds suitable for the practice of this invention can be synthesized by those skilled in the art using any appropriate synthesis technique.

The alkylmagnesium compound used must be selected to result in the appropriate alkyl group being transferred to the sulfonate ester. For example, if cis-oleyl alcohol were to be reacted by the present invention to cis-9-tricosene, an n-pentylmagnesium compound such as those selected from the group consisting of n-pentylmagnesium chloride, n-pentylmagnesium bromide, and n-pentylmagnesium iodide would be employed as the alkylmagnesium halide to alkylate the sulfonate ester of oleyl alcohol. The preferred alkylmagnesium halide for the alkylation of oleyl alcohol to cis-9-tricosene is n-pentylmagnesium chloride.

A wide variety of alkylation catalysts are capable of promoting the alkylation of the sulfonate ester with the alkylmagnesium compound. The present invention is not limited to the use of a specific alkylation catalyst but any alkylation catalyst that will promote the alkylation of the sulfonate ester with alkylmagnesium compound so as to produce cis-olefins can be used. Suitable alkylation catalysts include, but are not limited to: cuprous salts selected from the group consisting of cuprous bromide, cuprous chloride, cuprous iodide, and dilithium cuprous tetrachloride. The preferred cuprous salt is cuprous bromide.

The alkylation catalyst can be employed in any suitable amount that will facilitate the alkylation of the sulfonate ester with the alkylmagnesium compound so as to produce cis-olefin. Generally the ratio of the moles of sulfonate ester to the moles of alkylation catalyst is in the range of about 1:1 to about 1:0.005. Preferably the ratio is in the range of about 1:0.01 to about 1:0.05.

Although the second reaction product, said sulfonate ester and the alkylmagnesium compound can be reacted together in about any the stoichiometric ratio of sulfonate ester to alkylmagnesium compound will generally be in the range of about 10:1 to about 1:10, and preferably the ratio is in the range of about 1:1 to about 1:2.

The alkylation of sulfonate ester with alkylmagnesium halide and cuprous salt alkylating catalyst can take place under a variety of reaction conditions. Generally the temperature of the alkylation will be in the range of about $-70°$ C. to about 10° C. Preferably the temperature is in the range of about $-30°$ C. to about 10° C., and most preferably in the range of about $-10°$ C. to about 5° C. In this alkylation step, pressure is not critical, but will generally be in the range of about 0 psig to about 2,000 psig. Preferably the pressure is in the range of about 0.1 psig to about 250 psig, and most preferably in the range of about 1 psig to about 25 psig.

The time of the alkylation of sulfonate ester with alkylmagnesium compound will depend upon the desired degree of conversion, the reaction temperature and concentration of sulfonate ester to alkylmagnesium compound, and the alkylation catalyst utilized, but will generally depend on the speed at which the three reaction components of this step can be mixed while still keeping the reaction mixture within the recommended temperature ranges. Preferably, the time is in the range of about 1 minute to about 360 minutes, most preferably in the range of about 5 minutes to about 120 minutes.

The preceeding three step processes will take place in a wide variety of organic solvents. Generally any organic solvent in which the reactants are soluble will be suitable. Preferably ethers such as tetrahydrofuran and diethyl ether are used as solvents. Currently preferred are organic solvents which include, but are not limited to, organic liquids selected from the group consisting of diethyl ether, methylpropyl ether, ethylpropyl ether, 2-methoxyethyl ether, and tetrahydrofuran.

The process of this invention may also be performed sequentially in one vessel. Those skilled in the art will recognize that the reactants should be utilized in ratios at each step which will be close to the stoichiometric ratios, thereby avoiding the possibility of side reactions which could interfere with the succeeding step in this process. The process of this invention should be practiced in the substantial absence of $O_2$, $CO_2$, and water to avoid inactivation of the alkylmagnesium compound of the third step.

The third reaction product will be prodominately (>50%) a cis-olefin. However, it may be desirable to recover this compound in a highly purified form. Prior to purification of the third reaction product, a preliminary work up would be performed, consisting of an acid wash which effects a phase separation, followed by a weak or diluted base, which effects a second phase separation. The third reaction product after being worked up must be further treated by either a second wash or silica gel chromatography. The second wash preferably will consist of an aqueous methanol solution: one part methanol to one part water with from about 1 to about 3 molar KOH in solution. The worked up third reaction product is then washed with the previously described aqueous KOH/methanol solution and the organic solution is rotor evaporated with the residue containing the cis-olefin then being recovered. The preferred method of recovery is distillation, but other methods of further purification or recovery known to those skilled in the art may be employed.

The following non-limiting example is provided to further illustrate the practice of the present invention.

EXAMPLE I

Synthesis of Cis-9-Tricosene

A 12 l flask equipped with a reflux condenser, Firestone valve, mechanical stirrer, and addition funnel was flushed with $N_2$. 500 g of oleyl alcohol and 1500 ml of tetrahydrofuran were added to the flask and the reaction mixture was cooled to 0° C. 1330 ml of n-butyllithium (1.6M in hexane) was added dropwise while maintaining the temperature below 5° C. The addition of butyllithium was completed in approximately 45 min. 420.6 g of p-toluenesulfonyl chloride was then added and the temperature was increased to 35°–40° C. using a heating mantle. The temperature was held at 40° C. for 3 hr. The reaction mixture was then cooled to 0° C. using a dry ice/isopropanol bath. 10 g of cuprous bromide was added followed by the dropwise addition of 1120 ml of n-pentylmagnesium bromide (2.5M in diethyl ether). This addition was completed in 48 min and the temperature was maintained near 0° C. during this time. The reaction mixture was stirred for 1 hr following the addition of n-pentylmagnesium bromide, then warmed to room temperature and held overnight under $N_2$. 6.5 l of 4M HCl was added followed by phase separation. The organic phase was washed with 3 l of saturated sodium bicarbonate solution, followed by 2 volumes of a 1M KOH/MeOH solution (an aqueous KOH/MeOH solution as prepared by mixing one part of methanol and one part of water, with a final KOH concentration of 1M) the aqueous phase is then decanted. The organic solvent was removed by rotor evaporation and the residue distilled at 0.1 mm Hg vacuum. The distilled yield based on pure oleyl alcohol was 92.3%, with the final product containing 75% cis isomer.

That which is claimed is:

1. A process for the synthesis of a cis-olefin from a cis-olefinic alcohol consisting essentially of the following steps:
   (a) reacting a cis-olefinic alcohol with a source of alkali metal ion selected from the group consisting of lithium and sodium ions to form a first reaction product
   (b) then contacting said thus formed first reaction product with a sulfonyl halide compound wherein the sulfonyl halide compound is selected from the group consisting of an alkyl sulfonyl halide and an aryl sulfonyl halide wherein the halide of said sulfonyl halide compound is selected from the group consisting of chloride and bromide to form a second reaction product,
   (c) then contacting said thus formed second reaction product with a cuprous salt and alkylmagnesium compound selected from the group consisting of dialkylmagnesium and alkylmagnesium halide wherein the halide of said alkylmagnesium halide is selected from the group consisting of iodide, bromide, and chloride to form a third reaction product comprising a cis-olefin wherein the steps are carried out in a suitable organic solvent.

2. A process according to claim 1 wherein the alkali metal source selected from the group consisting of sodium metal, lithium metal, alkyllithium, aryllithium, alkylsodium, and arylsodium.

3. A process according to claim 2 wherein said alkyllithium is selected from the group consisting of phenyllithium, butyllithium, and methyllithium.

4. A process according to claim 1 wherein said sulfonyl halide compound is selected from the group consisting of p-toluenesulfonyl halide, o- and p-toluenesulfonyl halide, methylsulfonyl halide, trifluoromethane sulfonyl halide, and benzene sulfonyl halide wherein the halide is selected from the group consisting of chloride and bromide.

5. A process according to claim 1 wherein the alkylmagnesium compound is an alkylmagnesium halide.

6. A process according to claim 1 wherein the cuprous salt is selected from the group consisting of cuprous bromide, cuprous iodide, cuprous chloride, cuprous cyanide, and dilithium cuprous tetrachloride.

7. A process according to claim 6 wherein the cuprous salt is cuprous bromide.

8. A process according to claim 1 wherein the synthesis is performed in one reaction vessel.

9. A process according to claim 1 wherein reacting a cis-olefinic alcohol with an alkali metal is performed within a temperature range from about −70° C. to about 50° C.

10. A process according to claim 1 wherein the contacting of the first reaction product with a sulfonyl halide compound is performed between about 0° C. to about 70° C.

11. A process according to claim 1 wherein the contacting of the second reaction product with an alkylmagnesium compound is performed between about −70° C. to about 10° C.

12. A process for the synthesis of a cis-olefin from a cis-olefinic alcohol consisting essentially of the following steps:
   (a) reacting a cis-olefinic alcohol with an alkyllithium wherein the temperature ranges are from about −70° C. to about 50° C. to form a first reaction product
   (b) then contacting said thus formed first reaction product with a sulfonyl halide compound wherein the sulfonyl halide compound is selected from the group consisting of an alkyl sulfonyl halide and an aryl sulfonyl halide wherein the halide of said sulfonyl halide compound is selected from the group consisting of chloride and bromide wherein the temperature ranges are from about 0° C. to about 70° C. to form a second reaction product,
   (c) then contacting said thus formed second reaction product with a cuprous salt and an alkylmagnesium compound selected from the group consisting of dialkylmagnesium and alkylmagnesium halide wherein the halide of said alkylmagnesium halide is selected from the group consisting of iodide, bromide, and chloride wherein the temperature ranges are from about −70° C. to about 10° C. to form a third reaction product comprising a cis-olefin wherein the steps are carried out in a suitable organic solvent selected from the group consisting of diethylether, methylpropyl ether, ethylpropyl ether, 2-methoxyethyl ether, and tetrahydrofuran.

13. A process according to claim 12 wherein the alkyllithium is n-butyllithium.

14. A process according to claim 12 wherein the sulfonyl halide compound is p-toluenesulfonyl halide.

15. A process according to claim 12 wherein the sulfonyl halide compound is p-toluenesulfonyl chloride.

16. A process according to claim 12 wherein the cuprous salt is cuprous bromide.

17. A process according to claim 12 wherein the olefinic alcohol is cis-oleyl alcohol.

18. A process according to claim 12 wherein the alkylmagnesium compound is n-pentylmagnesium bromide.

19. A process according to claim 12 wherein the third reaction product is cis-9-tricosene.

20. A process according to claim 12 wherein said organic solvent is tetrahydrofuran.

21. A process according to claim 12 wherein the synthesis is performed in one reaction vessel.

* * * * *